(12) United States Patent
Bochner

(10) Patent No.: US 6,271,022 B1
(45) Date of Patent: Aug. 7, 2001

(54) DEVICE FOR INCUBATING AND MONITORING MULTIWELL ASSAYS

(75) Inventor: Barry Bochner, Alameda, CA (US)

(73) Assignee: Biolog, Inc., Hayward, CA (US)

( * ) Notice: Subject to any disclaimer, the term of this patent is extended or adjusted under 35 U.S.C. 154(b) by 0 days.

(21) Appl. No.: 09/277,353

(22) Filed: Mar. 26, 1999

Related U.S. Application Data

(63) Continuation-in-part of application No. 09/267,039, filed on Mar. 12, 1999, now abandoned.

(51) Int. Cl.[7] .................................................. C12M 1/34
(52) U.S. Cl. .................................. 435/287.3; 435/288.7; 422/65; 422/82.05; 356/388; 356/395; 382/128; 382/133
(58) Field of Search ........................ 422/63, 65, 68.1, 422/50, 52, 82.05, 82.08, 82.09; 435/287.3, 288.7; 356/51, 302, 346, 388, 395, 244; 382/128, 133

(56) References Cited

U.S. PATENT DOCUMENTS

| | | | |
|---|---|---|---|
| D. 377,455 | 1/1997 | Burchard et al. | D10/81 |
| D. 382,647 | 8/1997 | Staples et al. | D24/216 |
| 3,773,426 | 11/1973 | Mudd | 356/205 |
| 4,129,483 | 12/1978 | Bochner | 195/100 |
| 4,234,833 | 11/1980 | Barrett | 318/282 |
| 4,235,964 | 11/1980 | Bochner | 435/34 |
| 4,529,920 | 7/1985 | Yoshida et al. | 318/466 |
| 4,720,463 | 1/1988 | Farber et al. | 435/291 |
| 4,724,215 | 2/1988 | Farber et al. | 435/291 |
| 4,817,785 | 4/1989 | Farber et al. | 198/803.01 |
| 4,823,156 | 4/1989 | Shrader et al. | 354/115 |
| 4,856,073 | 8/1989 | Farber et al. | 382/6 |
| 5,134,063 | 7/1992 | Bochner | 435/29 |
| 5,469,141 | 11/1995 | Ghazarian | 340/566 |
| 5,589,350 | 12/1996 | Bochner | 435/29 |
| 5,627,045 | 5/1997 | Bochner et al. | 435/34 |
| 5,670,375 | 9/1997 | Seaton et al. | 436/48 |
| 5,697,409 | 12/1997 | Bishop et al. | 141/284 |
| 5,762,873 | 6/1998 | Fanning et al. | 422/65 |
| 5,766,553 | 6/1998 | Staples et al. | 422/102 |
| 5,774,179 | 6/1998 | Chevrette et al. | 348/218 |
| 5,798,084 | 8/1998 | Seaton et al. | 422/65 |
| 5,798,085 | 8/1998 | Seaton et al. | 422/65 |
| 5,800,785 | 9/1998 | Bochner | 422/102 |
| 5,843,380 | 12/1998 | Staples et al. | 422/102 |
| 5,853,666 | 12/1998 | Seaton et al. | 422/65 |
| 5,853,667 | 12/1998 | Seaton et al. | 422/65 |
| 5,882,882 | 3/1999 | Bochner et al. | 435/34 |
| 5,888,825 | 3/1999 | Carr et al. | 436/48 |
| 6,046,021 | 4/2000 | Bochner | 435/34 |
| 6,136,534 | 10/2000 | Bochner | 433/34 |

OTHER PUBLICATIONS

U.S. application No. 09/116,078, Bochner et al, filed Jul. 15, 1998.

B.R. Bochner, "Sleuthing Out Bacterial Identities," *Nature*, 339:157–158 (1989).

B.R. Bochner, "Breathprints" at the Microbial Level: An Automated Redox–Based Technology Quickly Identifies Bacterial According to Their Metabolic Capacities, *ASM News* 55:536–539 (1990).

B. Bochner and M. Savageau, "Generalized Indicator Plate for Genetic, Metabolic, and Taxonomic Studies with Microorganisms," *Appl. Environ. Microbiol.*, 33:434–444 (1977).

Primary Examiner—David A. Redding
(74) Attorney, Agent, or Firm—Medlen & Caroll, LLP

(57) ABSTRACT

The present invention provides easy-to-use, adaptable, and convenient solutions to a heretofore unmet need for instruments that can incubate and kinetically monitor assays, especially multiwell assays. In particular, the present invention finds use in monitoring assays contained within various test formats, including, but not limited to microtiter plates, miniaturized test panels (e.g., MICROCARDS™), and petri plates.

32 Claims, 3 Drawing Sheets

DEVICE FOR INCUBATING AND MONITORING MULTIWELL ASSAYS

This application is a continuation-in-part of 09/267039 filed Mar. 12, 1999, now abandoned.

FIELD OF THE INVENTION

The present invention provides easy-to-use, adaptable, and convenient solutions to a heretofore unmet need for an instrument that can incubate and kinetically monitor assays, especially multiwell assays. In particular, the present invention finds use in monitoring assays contained within various test formats, including, but not limited to microtiter plates, miniaturized test panels (e.g., MICROCARDS™), and petri plates.

BACKGROUND OF THE INVENTION

Various methods are available to analyze biological samples using optical analyses, including reflective and transmitted light, fluorescence, and luminescence. The purpose of the analysis is often to assay the response of cells, for example, to the presence of a chemical (e.g., a nutrient, hormone, antibiotic, pharmaceutical, toxic chemical, etc.).

However, methods and devices in use to date are generally limited in terms of their mechanical reliability, easy of use, capacity, speed, expense, and format flexibility. For example, devices currently in use are only capable of monitoring certain, specific formats, and are not capable of being adapted for use with multiple formats such as various microtiter plates (e.g., 96-, 384-, and 1536-well plates) or petri plates. All existing readers read one multiwell assay plate at a time. In addition, most or all available readers have an optical system which reads one row of a multiwell test panel at a time. Some examples of instruments that incubate and read a large number of multiwell plates are the Vitek (See e.g., 5,762,873, 5,853,667, 5,853,666, 5,798,085, 5,798,084, 5,670,375, 5,843,380, 5,766,553, D382,647, 5,697,409), MicroScan, and Sensititre instruments. The Vitek and MicroScan instruments have complex mechanisms for sliding out each plate, one at a time, for reading, and then sliding it back onto its shelf, while Sensititre has a single reading station, with an elevator transport system that moves each plate, one at a time, first onto the elevator, then to the reading station, and then back to its shelf. While these features allow for the analysis of multiple plates, the mechanisms are inefficient and are not capable of use with multiple formats. Thus, a need exists for improved instruments that increase mechanical reliability, easy of use, capacity, speed, affordability, and flexibility with multiple formats.

SUMMARY OF THE INVENTION

The present invention provides easy-to-use, adaptable, and convenient solutions to a heretofore unmet need for an instrument that can incubate and kinetically monitor assays, especially multiwell assays. In particular, the present invention finds use in monitoring assays contained within various test formats, including, but not limited to microtiter plates, miniaturized test panels (e.g., MICROCARDS™), and petri plates.

The present invention provides an instrument comprising: 1) an enclosure cabinet; 2) a plurality of sliding shelves mounted in said cabinet, wherein said shelves are capable of holding one or more assay plates; 3) an imaging device mounted in said cabinet for simultaneously capturing within a field of view one or more images of two or more of said assay plates located on one or more of said shelves; and 4) a means for moving said imaging device, whereby said imaging device can be selectively positioned, without moving said assay plates on said shelves, to simultaneously capture images of all wells in said field of view of said assay plates located on any of said shelves.

In some preferred embodiments the shelves have a dimension of approximately eight by eight inches, to facilitate use on laboratory benches, although the present invention is not limited to any particular size of shelves. In other preferred embodiments, the plurality of sliding shelves consists of at least twenty sliding shelves, although a greater or fewer number of shelves is contemplated by the present invention. In particularly preferred embodiments, the shelves are capable of holding at least two assay plates. For example, the assay plates can be multiwell assay plates or petri plates, although the present invention is not limited by type of assay plate used. In other embodiments, the shelves contain one or more openings for viewing at least one multiwell assay plate from the bottom of the shelves. The shelves may also contain one or more thumbholes to facilitate loading and unloading of the sample plates.

In some embodiments, the imaging device comprises a camera. In preferred embodiments, the camera is selected from the group consisting of a CCD camera and a CMOS camera. In other embodiments the imaging device comprises a scanner, although it is not intended that the present invention be limited by the type of imaging device used. In some embodiments, the means for moving the imaging device comprises a motor. For example, the present invention contemplates motors including, but not limited to, a stepper motor.

In some embodiments of the present invention, the cabinet is a temperature controlled incubator. In preferred embodiments, the cabinet is gas-tight and can maintain a controlled level of a gas. In yet other embodiments, the cabinet comprises an access door, and in particular embodiments, the shelves are accessible from the door.

In some embodiments of the present invention, the instrument further comprises a means for controlling the instrument. For example, in some embodiments, the means for controlling the instrument controls elements of the instrument selected from the group consisting of: internal temperature of the cabinet, internal lighting of the cabinet, internal gas composition of the cabinet, positions of the plurality of sliding shelves, position of the imaging device, activity of the means for moving the imaging device, imaging by the imaging device, door closing, door opening, and combinations thereof. In preferred embodiments, the means for controlling the instrument comprises a computer. In some embodiments, the computer is connected to the instrument by a standard RS-232 interface. In particularly preferred embodiments, the computer comprises electronics for receiving digital image information from said imaging device. In yet other preferred embodiments, the computer monitors, records data on, and/or controls elements of the instrument selected from the group consisting of: internal temperature of the cabinet, internal lighting of the cabinet, internal gas composition of the cabinet, positions of the plurality of sliding shelves, position of the imaging device, activity of the means for moving the imaging device, imaging by the imaging device, door closing, door opening, and combinations thereof. In other embodiments, the computer records data on the images of the assay plates.

The present invention further provides an instrument comprising: 1) an enclosure cabinet; 2) a plurality of sliding shelves mounted in the cabinet, wherein the shelves are capable of holding two or more assay plates; and 3) an imaging device mounted in the cabinet for capturing one or more images of the two or more assay plates located on each of said shelves, wherein each of the images captures all of the assay plates on any one or more of the shelves.

The present invention also provides a system comprising: 1) an enclosure cabinet; 2) a plurality of sliding shelves mounted in the cabinet; 3) two or more assay plates located on at least one of the sliding shelves; and 4) an imaging device mounted in the cabinet for simultaneously capturing within a field of view one or more images of the two or more assay plates. In some embodiments, the system further comprises 5) a means for moving the imaging device, whereby the imaging device can be selectively positioned, without moving the assay plates on the shelves, to simultaneously capture images of all wells in the field of view of the assay plates located on any of the shelves.

The systems and devices of the present invention find use in methods for kinetically monitoring assay plates. For example, the present invention provides a method comprising: providing a system comprising: 1) an enclosure cabinet; 2) a plurality of sliding shelves mounted in the cabinet; 3) two or more assay plates located on at least one of the sliding shelves; and 4) an imaging device mounted in the cabinet for simultaneously capturing within a field of view one or more images of the two or more assay plates; and capturing one or more images of the two or more assay plates using the imaging device, at two or more separate time points. In some methods of the present invention, the system further comprises a means for moving the imaging device, whereby the imaging device can be selectively positioned, without moving the assay plates on the shelves, to simultaneously capture images of all wells in the field of view of the assay plates located on any of the shelves.

DESCRIPTION OF THE INVENTION

The present invention provides easy-to-use, adaptable, and convenient solutions to a heretofore unmet need for an instrument that can incubate and kinetically monitor assays, especially multiwell assays. In particular, the present invention finds use in monitoring assays contained within various test formats, including, but not limited to microtiter plates, miniaturized test panels (e.g., MICROCARDS™; such as those described in U.S. Pat. Nos. 5,589,350 and 5,800,785, herein incorporated by reference), and petri plates. Importantly, the present invention provides a device that has a highly reliable mechanical design that is capable of incubating and reading quickly (e.g., every 15 minutes) a large number (e.g., 50) of microplates, is easy to load and unload, as well as featuring a compact design that takes up little bench space, is inexpensive to produce, and is adaptable so as to monitor multiwell plates with a variety of formats and physical shapes, including circular objects such as petri plates.

Although other instruments have been designed and are in use for incubating and monitoring multiwell assays (e.g., Vitek's machine, described in U.S. Pat. Nos. 5,762,873, 5,853,667, 5,853,666, 5,798,085, 5,798,084, 5,670,375, 5,843,380, 5,766,553, D382,647, 5,697,409 herein incorporated by reference, which uses special 30 and 45 well test cards, and MicroScan and Sensititre, both of which use nonstandard 96-well microplates), each of these devices do not solve the problems addressed by the present invention. In addition because of the moving parts required to move assay plates from one location to another, unlike the present invention, none of the instruments in current use are highly reliable and require frequent and expensive field servicing. Furthermore, all of these instruments are expensive to purchase as well as to maintain, and all are constrained to monitoring a single, specific multiwell assay plate.

GENERAL DESCRIPTION OF THE INVENTION

Figure 1:
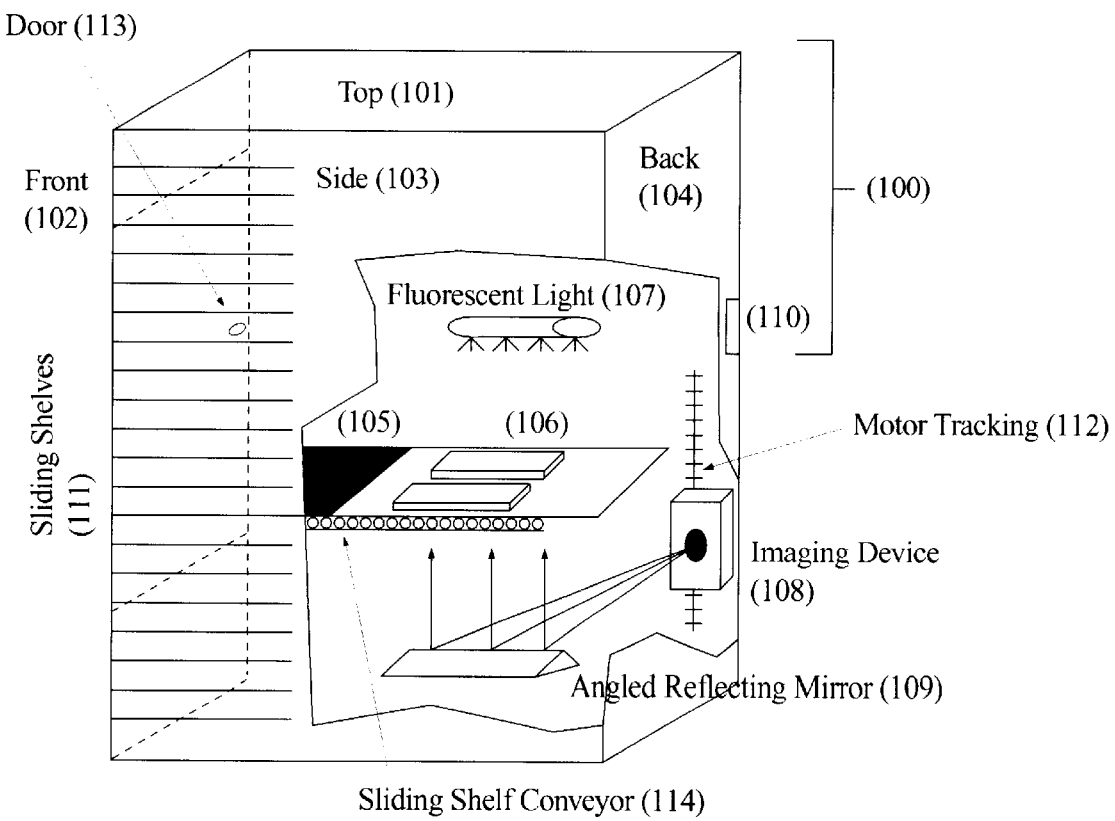
FIG. 1 is a perspective view, with parts broken away for clarity, of one embodiment of the present invention.
Figure 2:
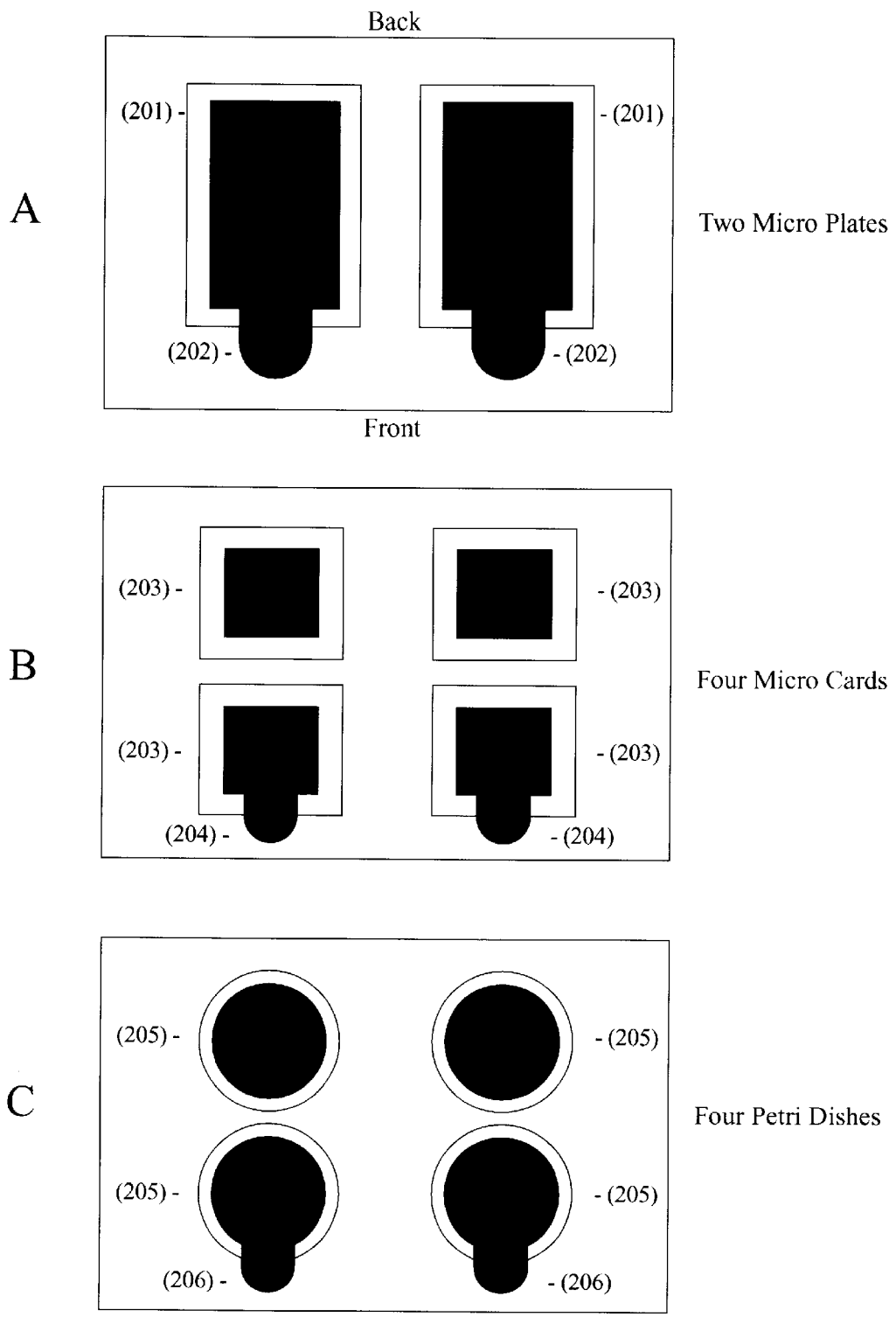
FIG. 2 is a schematic showing three alternative shelf formats, with Panel A showing a format for two microplates, Panel B showing a format for four MICROCARDS™, and Panel C showing a format for four petri plates.

The design of several embodiments of the present invention in shown in the FIGS. 1 and 2. The instrument of the present invention features multiple sliding shelves, each capable of holding a variety of sample assay formats (e.g., microtiter plates, miniaturized test systems such as MICROCARDS™, and petri plates, among others). The instrument also features a camera or other imaging device, designed to image the test samples on one or more of the shelves. Unlike currently available technologies, the imaging device of the present invention allow simultaneous imaging of all samples on a given shelf and allows imaging of each of the shelves without having to mechanically move each plate, one at a time, for reading.

The dimensions of the instrument are an important aspect of the present invention. The instrument is designed to fit within a laboratory setting, while minimizing the amount of surface area and work space occupied, yet providing interior space for incubation and analysis of multiple assay samples. In preferred embodiments, there are 25 shelves (111) with dimensions approximating 8×8 inches (i.e., 20×20 centimeters). Although the present invention is not limited to a specific size or shape, this shelf dimension is preferred for several reasons. First, this area is of a size that can be accurately imaged by imaging devices such as existing CCD (charge-coupled device) and CMOS (complementary metal oxide semiconductor) camera technology within a fairly small space. Thus, preferably, a camera or other imaging device (108) is placed about 8 inches (i.e., 20 cm) from the surface that is imaged in order to prevent significant parallax and distortion.

The camera technologies (i.e., existing CDD and CMOS technologies) are highly reliable, widely available, and inexpensive. Because these cameras have circular fields of view, they work best when viewing circular or square areas, as opposed to rectangular areas. Thus, as shown in the cross-sectional area of FIG. 1, two (2) standard microplates (106) can be placed on a shelf (105) of the present invention (e.g., 8×8 inch shelf) and viewed simultaneously by an imaging device such as a single camera (108). In some embodiments of the present invention, the camera may be mounted for movement and can be controlled to move into positions appropriate for the imaging of samples on different shelves. A mobile camera allows imaging of many samples without requiring removal of the samples from their shelves.

As shown in FIG. 2, the present invention is adaptable so as to allow the simultaneous monitoring of two standard microplates (201), or four (4) Biolog MICROCARDS™ (203) or four (4) standard petri plates (205), which can be placed on a shelf of the present invention (e.g., 8×8 inch shelf). As also shown in FIG. 2, in preferred embodiments of the present invention, thumbholes (202, 204, and 206) are provided in the shelves (111) to facilitate loading and unloading of the sample plates (201, 203, and 205).

The present invention provides significant advantages over currently used devices, as a unit with twenty-five (25) shelves (111) has the capacity to hold fifty (50) standard microplates or 100 Biolog MICROCARD™s or 100 standard petri plates. Furthermore, the present invention is capable of reading microplates that have virtually any number of wells (e.g., 24, 48, 96, 384, 1536, etc.), as well as single or multicompartment petri plates. The present invention can also be configured so as to contain interchangeable shelves that can hold a variety of multiwell assay plates, including a shelves designed to hold more than one type of assay plate. This is exemplary of the flexibility of capacity and adaptability for use in a commercial instrument. In addition to providing means for reading plates much faster, as two or more plates on a given shelf are read at a time, the present invention images and reads all wells in the field of view simultaneously and instantly.

The present invention addresses the space limitations of laboratories, as in preferred embodiments, dimensions for the overall size (i.e., to fit on a standard lab bench) indicate that the device should be no more than 36 inches high and 21 inches deep. An approximation of the actual dimensions of a 25-shelf instrument is 32 inches high, 21 inches deep, and 21 inches wide. Another reason that dimension is important is that if the shelf is 8 inches deep, and if it slides backward for reading, then the cabinet is already 8+8=16 inches deep. Since most standard lab benches are only 21 inches deep, the shelves of the present invention, in such cases, are designed to fit within a cabinet that allows placement of the cabinet on standard laboratory bench space.

In preferred embodiments, the cabinet (100) of the present invention comprises a biological incubator shell with accurate temperature control across a useful temperature range (e.g., 20–42° C.). There is a door (113) positioned in the front of the cabinet, to provide easy access to the shelves (111) which are loaded with samples (e.g., microplates, microcards, or petri dishes) by simply pulling a sliding shelf (105) forward. In preferred embodiments, the cabinet (100) is fitted with 25 shelves (111). When the cabinet door is closed, the cycle of viewing the assay plates (106) positioned on the shelves can begin. The sliding shelves (105) may slide either to the side or backward (i.e., in one preferred embodiment) and in doing so, the microwell assay plates (106) come into view of the imaging device (108) with one or more angled reflecting mirrors (109) being used to "fold" the light path and, in some embodiments, to direct the light to the camera's view. The plates (106) are imaged, and the digital image is transmitted to an attending computer (e.g., imaging system) (not shown in Figure) for data analysis and storage. In preferred embodiments, lighting is provided internally within the cabinet, by inexpensive, long-life lamps (107), including but not limited to fluorescent bulbs (e.g., F6T5), which are positioned above and/or below the shelves, in order to provide proper illumination. A variety of other long-life lighting devices are contemplated by the present invention, including, but not limited to, lamps that are known in the art for use in lighting notebook computer displays.

In addition, the cabinet of the present invention is preferably gas-tight, so that it can contain a controlled level of gas such as $CO_2$. It is also contemplated that the cabinet may be set up so as to be useful in the testing of anaerobic organisms. This novel capability finds use in assays in which the test cells or organisms require specialized atmospheres (e.g., elevated $CO_2$ levels, reduced oxygen tension, anaerobiosis, etc.).

In preferred embodiments, the camera (108) or other imaging device moves vertically (i.e., up and down) so as to be positioned properly every time it reads another shelf. The movement of the imaging device is accomplished through the use of a means for moving the imaging device such as a track (112) and a stepper motor. In a preferred embodiment (e.g., with microplates), the plates are viewed from their undersides (i.e., the camera views the bottom of the wells), as the lid of the microplates often become fogged or scratched during incubation and/or manipulation. By reading the microplates from the bottom, a clear view of the reaction in the wells is provided to the camera. As shown in FIG. 2, in some embodiments of the present invention, the shelves comprise openings (i.e., slots) whereby a portion of bottom surface area of the assay plates, represented by the shaded areas in FIG. 2, is open (i.e., viewable) from the bottom of the shelf. In such embodiments, the plates are supported on the shelf by a lip, as represented in FIG. 2 by the space between the shaded area and the surrounding black lines (i.e., the lines defining the edges of assay places [201], [203], and [205]). The shelves may further comprise thumbholes (202, 204, and 206) to facilitate loading and unloading of the sample plates.

However, in other embodiments, (e.g., for other applications, such as monitoring of petri plates), it may be preferred to have the camera view the sample area from the top and/or the side. In some preferred embodiments, the camera reads the wells or sample areas of the microplates, MICROCARDS™, or petri plates, and the images formed by the camera are processed by a processing means to determine test results (i.e., growth or no growth, susceptibility or resistance). Unlike other devices, such as that described in U.S. Pat. Nos. 4,856,073, 4,724,215, 4,270,463, and 4,817,785, all of which are herein incorporated by reference, the imaging device of the present invention is positioned such that it moves either horizontally or vertically within the cabinet. This allows the imaging device to be positioned in the optimum location to obtain images and therefore results, that are clear, easily readable, and easily analyzed.

The present invention also provides means to easily load and unload the sample plates. In contrast to other devices currently in use, which have single plate shelving arrangements tailored to the dimension of a specific plate, in some embodiments, the present invention's pull-out shelves (111) are made to be removable and interchangeable for different types of plates, providing scientists with the same degree of flexibility that they have in a standard incubator. Having this flexibility makes the instrument more versatile for performing a variety of research projects, and also expands the number of applications for the instrument. Furthermore, in preferred embodiments, the present invention has only simple one-dimensional mechanical motion. The sliding shelves (111) slide back and forth horizontally, and the imaging device (108) preferably moves up and down vertically. This simple design is more reliable and less expensive than other systems currently in use (e.g., systems where the sample plates are mechanically moved, one at a time, into position for imaging).

With any of the testing formats (e.g, microtiter plates, MICROCARD™, and petri plates, among others), the visual result that is detected by the device of the present invention can be any optically perceptible change such as a change in turbidity, a change in color, or the emission of light, such as by chemiluminescence, bioluminescence, or by Stokes shift. Color indicators may be, but are not limited to, redox indicators (e.g., tetrazolium and redox purple), pH indicators, chromogenic substrates or various dyes and the like. Various dyes are described in U.S. Pat. Nos. 4,129,483, 4,235,964 and 5,134,063 to Barry R. Bochner, hereby incorporated by reference (See also B. R. Bochner, Nature 339:157 [1989]; and B. R. Bochner, ASM News 55:536 [1990]). A generalized indicator useful for practice of the present invention is also described by Bochner and Savageau (See, B. Bochner and M. Savageau, Appl. Environ. Microbiol., 33:434 [1977]). Various formats for isolation and identification of organisms are also described in U.S. Pat. No. 5,627,045, and pending U.S. patent appln. Ser. Nos. 08/762,656, 09/116,078, and 09/098,066, all of which are herein incorporated by reference.

In some embodiments of the present invention, testing is based on redox technology. Testing based on the redox technology is extremely easy and convenient to perform. A cell suspension is prepared and introduced into the testing compartments of the device (e.g., wells of microtiter plates placed on a shelf of the present invention). Each compartment is prefilled with a different substrate. In a preferred embodiment, all wells are prefilled with test formula comprising a basal medium that provides nutrients for the microorganisms, and a color-change indicator, and each compartment is prefilled with a different carbon compound or "testing substrate," against which the microorganism is tested. "Basal medium," as used herein, refers to a medium which provides nutrients for the microorganisms, but does not contain sufficient concentrations of carbon compounds to trigger a color response from the indicator. "Carbon compound," "carbon source" and "testing substrate" are equivalent terms, and are used interchangeably herein to refer to a carbon chemical in sufficient concentration as to trigger a color response from the indicator when it is utilized (metabolized) by a microorganism (e.g., GN, GP, YT, and other MICROPLATES™ commercially available from Biolog) (See e.g., U.S. Pat. No. 5,627,045, and pending U.S. patent appln. Ser. Nos. 08/62,656, 08/421,377, 09/116,078, and 09/098,066, all of which are herein incorporated by reference).

Also in preferred embodiments, the entire operation of the instrument, including the movement of the shelves (105) and any movement of the imaging device (108), is preferably controlled by a standard, inexpensive desktop or notebook computer with video acquisition capability. Also in preferred embodiments, the computer monitors and/or controls temperature, camera function (e.g. focus and positioning), door closure, and data acquisition and analysis. However, it is contemplated that in other embodiments, multiple computers may be used for various purposes associated with the invention. Thus, it is not intended that the present invention be limited to any particular type or number of computers or automation systems.

DETAILED DESCRIPTION OF THE INVENTION

In preferred embodiments, the present invention provides a temperature-controlled, thermally-insulated cabinet (100), with external dimensions kept as small as possible (e.g., less than 36" high and 21" deep), to minimize the footprint of the device and conserve valuable laboratory space. The internal temperature of the cabinet is preferably adjustable within a range of about 20° C.–42° C., most preferably about 25° C.–37° C. with a controllable accuracy of +/–1° C. The cabinet of the present invention is also provided with means of air circulation, so as to prevent the formation of thermal gradients inside the chamber. However, the design of the cabinet allows air motion to be kept at a minimum, and away from the microplates, or other sample format. This prevents the drying of liquid contents within the test samples by air convection. In particularly preferred embodiments, the cabinet of the present invention is designed to be gas tight when closed, with an allowance for an inlet port and control valve system so that it can be attached to a $CO_2$ or anaerobic gas mixture cylinder and used with cells that require elevated $CO_2$ or anaerobiosis.

In preferred embodiments, the left side of the chamber (i.e., the front [102], as shown in FIG. 1) contains 25 horizontally sliding shelves (111), preferably with dimensions of approximately 8 in.×8 in. each, although fewer or greater numbers of shelves are contemplated by the present invention. Thus, as shown in FIG. 2, each shelf (111) is designed to hold two standard footprint microplates (201) and/or up to four standard footprint MICROCARDS™ (203), and/or petri plates (205). These shelves are accessible for random access batch loading through a door (113) on the left front face (102) of the instrument. The door (113) is fitted with a sensor so that opening the door automatically causes an interrupt (See e.g., U.S. Pat. Nos. 5,469141; 4,529,920; and 4,234,833). The interrupt stops all instrument motion (e.g., any movement of the camera and/or shelves is halted upon opening of the door).

In one preferred embodiment, a shelf (105) slides horizontally to come into the view of a camera-based imaging system (108 and 109), as shown in FIG. 1. The shelves slide either left-to-right or front-to-back. The sliding of the shelves can be automated and, optionally, can be tied to the movement of the imaging device. For example, as the imaging device moves vertically, to come into the appropriate range for imaging assay plates on the desired shelf, the motor for moving the imaging device positions a mechanical device for moving the shelf into position for imaging (i.e., a shelf sliding mechanism (114) capable of moving the shelves horizontally in and out, such as into and out of the field of view). However, the movement of the shelves need not be linked to the movement of the imaging device and the present invention contemplates embodiments where either the imaging device or the shelves need not be mobile. In another preferred embodiment, a camera or other imaging device is vertically positionable so that it can image the 8 inch×8 inch area covered by the two microplates loaded onto a shelf (105), viewing the microplates from underneath. In other embodiments, multiple (i.e., more than one) cameras or other imaging devices are used. The imaging device is preferably a motion and vibration insensitive color camera (i.e., solid state) such as, for example, a CCD (charge-coupled device) or CMOS (complementary metal oxide semiconductor) camera from an established, reliable manufacturer (e.g. Cohu, Toshiba) fitted with a good quality wide angle lens (e.g. Fujinon, Kowa). In particularly preferred embodiments, a Toshiba IK-M30AK or IK43S, CCD color camera is used. However, it is not intended that the present invention be limited to any particular camera and/or lens. It is also not intended that the present invention be limited to any specific configuration of camera and/or light path(s). Thus, it is contemplated that in some embodiments, the light path is curved or deviated using mirrors (e.g., planar or curved mirrors) (109), in order to most efficiently utilize the space within the cabinet and concomitantly maintain a small cabinet size.

In other embodiments of the present invention, a scanner is used in place of, or in combination with, the camera or other imaging device. The scanner can be positioned, such that individual shelves are within the scan range of the scanner. In some embodiments, the shelves can be moved into the scan range, while in other embodiments the scanner can be moved into a position whereby imaging of the samples on the shelves is facilitated. The present invention contemplates the use of a variety of scanner types. For example, the present invention contemplates the use a Microcontrolled Image Scanner (Peripheral Dynamics, Inc.; Plymouth Meeting, Pa.).

The video output of the camera, scanner, or other imaging device is sent to a computer via a frame grabber board (e.g. Nogatech, Matrox). It is contemplated that for most applications, a complete cycle to image all 25 shelves (111) of the unit should take no more than 15 minutes (i.e., less than 36 seconds per shelf). It is also contemplated that the output be configured so as to allow bar code reading of the samples. In these embodiments, it is further contemplated that the bar code information is provided (e.g., transmitted) to the computer with the sample information for storage and/or analysis.

In preferred embodiments of the present invention, the camera-based viewing system or other imaging system is moved through a plane (e.g., vertical plane) to allow automated imaging and analysis of samples on one or more shelf (111). The imaging system (108 and 109) comprises an imaging device and means coupled to the imaging device for moving the imaging device a predetermined amount, a plurality of times, and on a predetermined plane perpendicular to the sample plane (i.e., plane a shelf [105]) for providing an image at a plurality of different sample locations, and means for transmitting data for analysis and/or storage. In preferred embodiments, the imaging system is attached to a fixed base, which is movably mounted to the cabinet (100). A variable speed motor (e.g., a stepper motor) mounted between the fixed base and the cabinet (100) can move the camera-based viewing system over a limited range. Adjustably placeable limit switches can be used to sense preset limits of displacement and thereupon to stop the motor. Preferably, an electrical switching arrangement is provided for controlling the movement of the imaging system through a preset program, controlled by a computer.

It will be appreciated by those skilled in the art that servo mechanisms driven by relative position sensors, such as optical encoders, etc. may be used to provide the requisite relative motions of the camera-based viewing system with respect to the sample planes. In addition, such servo systems are readily providable by those skilled in the art in order to provide pan and tilt adjustments for the camera (108). Programmable microprocessor controllers are particularly well suited for controlling such servo systems within the optical environment of the inventive camera system.

In preferred embodiments of the present invention, the samples are illuminated using at least one light (107). In particularly preferred embodiments, approximately one or more 9 inch long fluorescent (e.g., F6T5 rod-shaped) bulbs are used. In other preferred embodiments, lamps used in notebook computers are used. In some embodiments of the present invention, the samples (e.g., microplate assays) are lit on both top and bottom surfaces (i.e., front lighting and back lighting). The lighting should be uniformly diffused over the approximately 8×8 inch area being optically monitored. In particularly preferred embodiments, access to the light bulb(s) (107) is provided by a door or an easily removed access panel (110) located on the back (104) as shown in FIG. 1, top (101), front (102), or side (103) of the cabinet. This door or access panel (110) also provides access to the interior of the cabinet, so as to allow the user to wipe away dust on lenses and mirrors, and do any types of routine repairs or adjustments needed on the camera viewing system. Thus, the present invention provides a device with an cabinet design that is configured so as to be as small and lightweight as possible, as well as maximize the lab bench space available, while also allowing easy access for service or repair of the components within the device.

In particularly preferred embodiments, the cabinet is provided with easily readable status lights to indicate the power status (i.e., power on/power off), the temperature inside the cabinet, and an interrupt. In other preferred embodiments, the status lights are useful in alerting the user if the environment within the cabinet has deviated from the desired conditions. For example, the temperature in the cabinet can be monitored, with temperature information sent to and analyzed by a computer or other processor. If the temperature deviates from a preset, desired range, a light is activated to alert the user that the temperature is out of the desired range. As the device will find use internationally, in preferred embodiments the status lights, bulbs, and power supply are configured so as to allow users in various countries to utilize the device as their needs dictate. For example, in alternative preferred embodiments, the power supply will accept either 110 or 220 volts and is designed to achieve a CE mark.

In some embodiments of the present invention, there is a signal processing and control unit for processing the images from the camera. In other embodiments, the signal processing and control unit also controls various other functions of the device (e.g., temperature, gas content, humidity, etc.). The signal processing part of the unit may include image processors such as the "System 20,000H" (Unitron Imagetek Systems, Plain View N.Y.), IP-512 (Imaging Technology Inc., Woburn Mass.), Model 1000 (Image Technology Corporation, Deer Park, N.Y.), Scan 78/99 (Eikonix Corporation, Bedford, Mass.), Datatech 565 (Datatech), and Model 109RM (LogE/Spatial Data Systems Goleta Calif.). In preferred embodiments, the signal processing unit delivers image information to a computer or other control processor, which not only analyses the images from the imaging device, but also determines from that analysis a partial test result for each well (or testing area), or results for each test panel (e.g., each microplate, MICROCARD™, or petri plate), and the total test result or results for each test panel.

Also in preferred embodiments, the signal processing and control unit controls the movement of the camera and/or sliding shelves. For example the signal processing and control unit includes control circuitry for controlling the operation involved in the movement of these components by activating motor drives that are capable of moving the camera and/or sliding drawers. For example, in some embodiments of the present invention, the signal processing and control unit includes a microcomputer suitably programmed to control the apparatus, while in other embodiments, hard-wired circuitry is used to control the apparatus, in particularly controlling the motor drives to move the various components of the device in a coordinated fashion.

In some embodiments, the control circuitry determines the position of the imaging device by means of Hall-effect sensors fixedly secured to a flange which is stationary with respect to the housing of the cabinet. A magnet is suitably mounted on a member which moves with the camera. There is a sensor that corresponds to each of the shelves, so that as the camera is raised or lowered, the Hall-effect sensors detect the magnet as the magnet is moved during the positioning of the camera.

Figure 3:
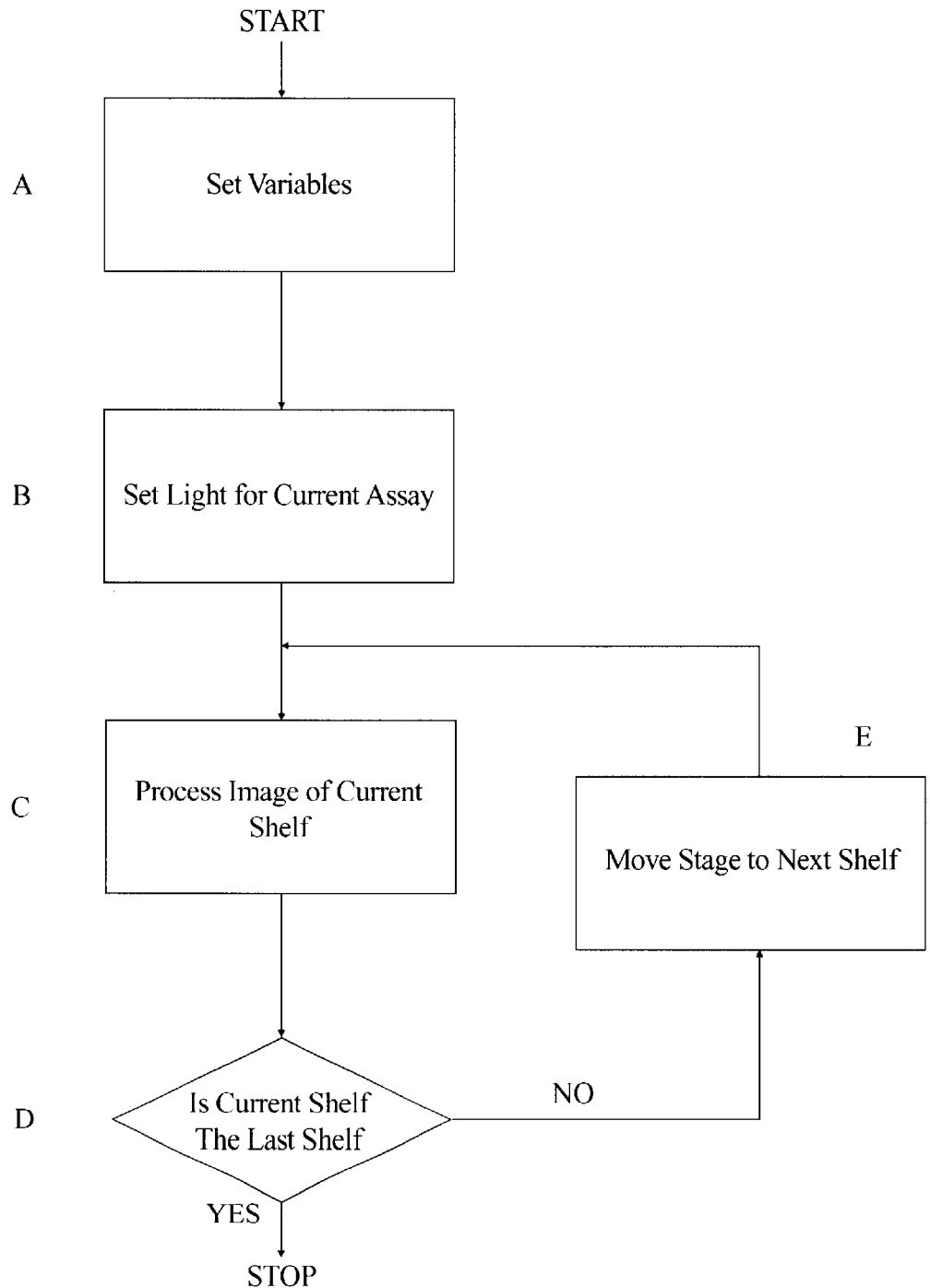
FIG. 3 illustrates a basic flowchart of the processing steps of the automated image analysis method of the present invention.

FIG. 3 illustrates a basic flowchart of the processing steps for some embodiments of the present invention. Specifically, at Step A, a user inputs various variables and configuration data which identify the assay being examined and several examination parameters. These variables include the assay number, temperature, the size thresholds and corresponding categories, flags for different save operations, instructions for post assay data analysis, and a standard luminance for the assays.

Step B of FIG. 3 corresponds to procedures for setting the light level for the current assay. This is to provide for a light setting that will provide for optimal luminance match-up for each assay. Luminance match-up may be beneficial so that the sample wells are examined under the same conditions.

Step C of FIG. 3 corresponds to procedures for processing the digitized images of samples on each shelf. In some embodiments of the present invention, once the computer captures an image of a specific shelf, specific enhancement procedures are executed to modify (e.g., clean and clarify) the image.

DEFINITIONS

The terms "sample" and "specimen" in the present specification and claims are used in their broadest sense. On the one hand, they are meant to include a specimen or culture. On the other hand, they are meant to include both biological and environmental samples. These terms encompasses all types of samples obtained from humans and other animals, including but not limited to, body fluids such as urine, blood, fecal matter, cerebrospinal fluid (CSF), semen, and saliva, as well as solid tissue. The terms also include, but are not limited to biochemicals, immunochemicals, and reagents. These terms also refers to swabs and other sampling devices which are commonly used to obtain samples for culture of microorganisms.

Biological samples may be animal, including human, cells, fluid or tissues, plant cells, fluids or tissues, microorganisms of all types, including bacteria and fungi, food products and ingredients such as dairy items, vegetables, meat and meat by-products, and waste. Environmental samples include environmental material such as surface matter, soil, water, and industrial samples, as well as samples obtained from food and dairy processing instruments, apparatus, equipment, disposable, and non-disposable items. These examples are not to be construed as limiting the sample types applicable to the present invention.

As used herein, the term "culture" refers to any sample or specimen which is suspected of containing one or more cell type. "Pure cultures" are cultures in which the cells present are only of one strain of a particular genus and species. This is in contrast to "mixed cultures," which are cultures in which more than one clonal type of cells are present.

As used herein, the term "organism" is used to refer to any species or type of microorganism, including but not limited to bacteria, yeasts and other fungi. As used herein, the term fungi, is used in reference to eukaryotic organisms such as the molds and yeasts, including dimorphic fungi.

As used herein, the terms "cell-inhibiting agent," "antimicrobial," or "toxic chemical" are used in reference to any compound which inhibits the growth of, or kills microorganisms or other types of cells. It is intended that the term be used in its broadest sense, and includes, but is not limited to compounds such as antibiotics, toxins, biocides, etc. which are produced naturally or synthetically. It is also intended that the term includes compounds and elements that are useful for inhibiting the growth of, or killing microorganisms or other types of cells.

As used herein, the terms "chromogenic compound" and "chromogenic substrate," refer to any compound useful in detection systems by their light absorption or emission characteristics. The term is intended to encompass any enzymatic cleavage products, soluble, as well as insoluble, which are detectable either visually or with optical machinery. Included within the designation "chromogenic" are all enzymatic substrates which produce an end product which is detectable as a color change. This includes, but is not limited to any color, as used in the traditional sense of "colors," such as indigo, blue, red, yellow, green, orange, brown, etc., as well as fluorochromic or fluorogenic compounds, which produce colors detectable with fluorescence (e.g., the yellow-green of fluorescein, the red of rhodamine, etc.). It is intended that such other indicators as dyes (e.g. pH) and luminogenic compounds be encompassed within this definition.

As used herein, the commonly used meaning of the terms "pH indicator," "redox indicator," and "oxidation-reduction indicator," are intended. Thus, "pH indicator" encompasses all compounds commonly used for detection of pH changes, including, but not limited to phenol red, neutral red, bromthymol blue, bromcresol purple, bromcresol green, bromchlorophenol blue, m-cresol purple, thymol blue, bromcresol purple, xylenol blue, methyl red, methyl orange, and cresol red. The terms "redox indicator" and "oxidation-reduction indicator" encompasses all compounds commonly used for detection of oxidation/reduction potentials (i.e., "eH") including, but not limited to various types or forms of tetrazolium, redox purple, resazurin, and methylene blue.

As used herein, the term "inoculating suspension" or "inoculant" is used in reference to a suspension which may be inoculated with cells to be tested. It is not intended that the term "inoculating suspension" be limited to a particular fluid or liquid substance. For example, inoculating suspensions may be comprised of water, saline, or an aqueous solution which includes at least one gelling agent (See e.g., pending U.S. patent appln. Ser. Nos. 08/762,656, 08/819, 452 and 09/116,078, all of which are herein incorporated by reference). It is also contemplated that an inoculating suspension may include a component to which water, saline, biochemical nutrients, chromogenic compounds, or any useful material is added. It is contemplated in one embodiment, that the component comprises at least one component useful for the intended cell culture. It is not intended that the present invention be limited to a particular component.

As used herein, the term "imaging device" refers to any device capable of capturing (i.e., replicating the visual image of a sample), and storing or transmitting images. Imaging devices include, but are not limited to cameras and scanners.

As used herein, the term "kit" or "panel" is used in reference to a combination of reagents and other materials.

As used herein, the term "carbon source" is used in reference to any compound which may be utilized (e.g., by cells) as a source of carbon for bacterial growth and/or metabolism. Carbon sources may be in various forms, including, but not limited to polymers, carbohydrates, acids, alcohols, aldehydes, ketones, amino acids, and peptides.

As used herein, the terms "nitrogen source," "phosphorus source," and "sulfur source," are used in reference to any compound which may be utilized respectively (e.g., by cells) as a source of nitrogen, phosphorus, or sulfur for growth and/or metabolism. As with carbon sources, nitrogen, phosphorus, and sulfur sources may be in various forms, including both inorganic and organic forms.

As used herein, the term "testing substrate" is used in reference to any carbon and/or nitrogen, phosphorus, or sulfur source that may be utilized to differentiate cells based on biochemical characteristics. For example, one cell type may utilize one testing substrate that is not utilized by another cell type. This utilization may then be used to differentiate between these two cultures. It is contemplated that numerous testing substrates be utilized in combination. Testing substrates may be tested individually (e.g., one substrate per testing well or compartment, or testing area) or in combination (e.g., multiple testing substrates mixed together and provided as a "cocktail").

Following exposure to a testing substrate such as a carbon, nitrogen, phosphorus, or sulfur source, or a cell-inhibiting agent, the response of a cell culture may be detected. This detection may be visual (i.e., by eye), or in preferred embodiments, accomplished with the assistance of the device of the present invention. For example, the response of cells to carbon sources may be detected as turbidity in the suspension due to the utilization of the testing substrate by the organisms. Likewise, growth can be used as an indicator that an organism is not inhibited by certain antimicrobials. In one embodiment, color is used to indicate the presence or absence of organism growth/metabolism.

As used herein, the terms "testing device," "test panel," and "assay plate," are used in reference to testing systems in which at least one cell type is tested for at least one test characteristic, such as utilization of a carbon source, nitrogen source, phosphorus source, sulfur source, or chromogenic substrate, and/or susceptibility to a cell-inhibiting agent. This definition is intended to encompass a microtiter plate having at least one gel-initiating agent (See e.g., pending U.S. patent appln. Ser. Nos. 08/762,656, 08/819,452 and 09/116,078, all of which are herein incorporated by reference) included in each of a plurality of wells or compartments, although in one embodiment, no gel initiating agent is used. It is also intended that other compounds such as carbon sources or cell-inhibiting agents will be included within the compartments. The definition is also intended to encompass a MICROCARD™ (Biolog; See e.g., U.S. Pat. Nos. 5,589,350 and 5,800,785) or other miniaturized plates or cards which are similar in function, but much smaller than standard microtiter plates (for example, many testing devices can be conveniently held in a user's hand). It is not intended that the present invention be limited to a particular size or configuration of testing device. For example, it is contemplated that various formats will be used with the present invention, including, but not limited to microtiter plates, microcards, petri plates (including compartmentalized plates with internal dividers used to separate different media placed within the plate), as well as many other formats.

Microtiter plates or "microplates" were introduced in the 1960's to facilitate laboratory testing in situations where a large number of tests were run simultaneously. The most typical microplates contain ninety-six (96) molded plastic wells (in an 8×12 array) with a typical sample volume capacity of about 0.2 milliliters. It is not intended that the assays of the present invention be carried out in a particular plate format; a range of well volumes (e.g., approximately 0.001 to 0.200 milliliters) is contemplated.

A wide variety of mechanical fluid handling devices are now available so that specimens, chemical solutions and other liquids can be transferred into the wells of microplates. Usually a row of eight (8) or twelve (12) wells are filled simultaneously, but some handling devices can simultaneously add sample to all of the wells. It is not intended that the present invention be limited to microplates made of particular materials, or to microwells of particular dimensions or volumes. In one embodiment, the microplate is made of a rigid plastic, such a polystyrene. The plastic can be clear or opaque. Also, the multiwell plate may have a side or bottom made of a filter material such as teflon.

In preferred embodiments, the microplates, MICROCARDS™, and/or petri plates are inoculated with the specimen(s) to be tested, and are then placed within the chamber for incubation, monitoring, and test analysis. At various times (e.g., at set time intervals programmed into the control and signal processing unit), the specimens are imaged by the imaging device. Thus, the present invention permits the essentially continuous monitoring of each sample during the incubation period. This provides advantages in diagnostic applications, because as soon as a test is read as a "positive," or a panel of tests is completed, the user can be alerted. In many cases, this increased speed in the time necessary to make a definitive diagnosis is of great importance in patient care, as appropriate antimicrobials or other treatment regimens may be instituted sooner in the course of the patient's disease than with other commonly used methods.

In summary, the present invention provides numerous advances and advantages over the prior art, including cost savings, reliability, adaptability to multiple formats, and a small footprint. All of these advantages enhance the convenience, speed, and accuracy of scoring test results in studies to characterize and/or identify microorganisms, and/or determine the susceptibilities of microorganisms to antimicrobial(s). It can also be applied to animal and plant cells, for example, to study growth stimulating (nutrient) and inhibiting (toxic) chemicals.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in diagnostic microbiology, cell biology, cell culture, immunology, immunochemistry, and nucleic acid probe assay methods, as well as device design and use, and/or related fields are intended to be within the scope of the following claims.

What is claimed is:

1. An instrument comprising: 1) an enclosure cabinet; 2) a plurality of sliding shelves mounted in said cabinet, wherein said shelves are capable of holding one or more assay plates; 3) an imaging device mounted in said cabinet for simultaneously capturing within a field of view one or more images of one or more of said assay plates located on one or more of said shelves; and 4) a means for moving said imaging device, whereby said imaging device can be selectively positioned, without moving said assay plates on said shelves, to simultaneously capture images of all wells in said field of view of said assay plates located on any of said shelves.

2. The instrument of claim 1, wherein said sliding shelves are capable of sliding into the field of view of said imaging device.

3. The instrument of claim 1, wherein said imaging device comprises a camera.

4. The instrument of claim 1, wherein said imaging device comprises a scanner.

5. The instrument of claim 1, wherein said cabinet is a temperature controlled incubator.

6. The instrument of claim 1, wherein said cabinet is gas-tight and can maintain a controlled level of a gas.

7. The intent of claim 1, wherein each of said shelves has a dimension of approximately eight by eight inches.

8. The instrument of claim 1, wherein said plurality of sliding shelves consists of at least twenty sliding shelves.

9. The instrument of claim 1, wherein one or more of said shelves are capable of holding at least two assay plates.

10. The instrument of claim 9, wherein said shelves contain one or more openings for viewing at least one multiwell assay plate from the bottom of said shelves.

11. The instrument of claim 9, wherein said shelves are capable of holding one or more assay plates selected from the group consisting of microplates, MICROCARDS™, and petri dishes.

12. The instrument of claim 1, wherein said cabinet comprises an access door.

13. The instrument of claim 12, wherein said shelves are accessible from said door.

14. The instrument of claim 3, wherein said camera is selected from the group consisting of a CCD camera and a CMOS camera.

15. The instrument of claim 1, wherein said means for moving said imaging device comprises a motor.

16. The instrument of claim 15, wherein said motor is a stepper motor.

17. The instrument of claim 1, further comprising a means for controlling said instrument.

18. The instrument of claim 17, where said means for controlling said instrument controls elements of said instrument selected from the group consisting of: internal temperature of said cabinet, internal lighting of said cabinet, internal gas composition of said cabinet, positions of said plurality of sliding shelves, position of said imaging device, activity of said means for moving said imaging device, imaging by said imaging device, door closing, door opening, and combinations thereof.

19. The instrument of claim 18, wherein said means for controlling said instrument comprises a computer.

20. The instrument of claim 19, wherein said computer is connected to said instrument by a standard RS-232 interface.

21. The instrument of claim 19, wherein said computer comprises electronics for receiving digital image information from said imaging device.

22. The instrument of claim 19, where said computer monitors elements of said instrument selected from the group consisting of: internal temperature of said cabinet, internal lighting of said cabinet, internal gas composition of said cabinet, positions of said plurality of sliding shelves, position of said imaging device, activity of said means for moving said imaging device, imaging by said imaging device, door closing, door opening, and combinations thereof.

23. The instrument of claim 19, where said computer records data on elements of said instrument selected from the group consisting of: internal temperature of said cabinet, internal lighting of said cabinet, internal gas composition of said cabinet, positions of said plurality of sliding shelves, position of said imaging device, activity of said means for moving said imaging device, imaging by said imaging device, door closing, door opening, and combinations thereof.

24. The instrument of claim 19, where said computer controls elements of said instrument selected from the group consisting of: internal temperature of said cabinet, internal lighting of said cabinet, internal gas composition of said cabinet, positions of said plurality of sliding shelves, position of said imaging device, activity of said means for moving said imaging device, imaging by said imaging device, door closing, door opening, and combinations thereof.

25. The instrument of claim 19, wherein said computer records data on the images of the assay plates.

26. An instrument comprising: 1) an enclosure cabinet; 2) a plurality of sliding shelves mounted in said cabinet, wherein said shelves are capable of holding two or more assay plates; and 3) an imaging device mounted in said cabinet for capturing one or more images of said two or more assay plates located on each of said shelves, wherein each of said images captures all of said assay plates on any one or more of said shelves.

27. The instrument of claim 26, wherein said sliding shelves are capable of sliding into a field of view of said imaging device.

28. The instrument of claim 26, further comprising 4) a means for moving said imaging device, whereby said imaging device can be selectively positioned, without moving said assay plates on said shelves, to simultaneously capture images of all wells in a field of view of said assay plates located on any of said shelves.

29. A system comprising: 1) an enclosure cabinet; 2) a plurality of sliding shelves mounted in said cabinet; 3) two or more assay plates located on at least one of said sliding shelves; and 4) an imaging device mounted in said cabinet for simultaneously capturing within a field of view one or more images of said two or more assay plates.

30. The system of claim 29, further comprising 5) a means for moving said imaging device, whereby said imaging device can be selectively positioned, without moving said assay plates on said shelves, to simultaneously capture images of all wells in said field of view of said assay plates located on any of said shelves.

31. A method for kinetically monitoring assay plates, comprising:

a) providing the system of claim 29; and b) capturing one or more images of said two or more assay plates using said imaging device, at two or more separate time points.

32. The method of claim 31, wherein said system further comprises a means for moving said imaging device, whereby said imaging device can be selectively positioned, without moving said assay plates on said shelves, to simultaneously capture images of all wells in said field of view of said assay plates located on any of said shelves.

* * * * *